United States Patent

Martin et al.

Patent Number: 5,749,520
Date of Patent: May 12, 1998

[54] LIQUID AIR FRESHENER DISPENSER DEVICE WITH CAPILLARY WICKING MEANS

[75] Inventors: John Martin, Caledonia; Eric J. Miller, Mt. Pleasant, both of Wis.

[73] Assignee: S. C. Johnson & Son, Inc., Racine, Wis.

[21] Appl. No.: 768,549

[22] Filed: Dec. 18, 1996

[51] Int. Cl.[6] .................................................. A61L 9/00
[52] U.S. Cl. ........................................ 239/44; 239/34
[58] Field of Search ........................... 239/145, 34, 35, 239/44, 45, 49, 57, 51.5; 261/99, 110

[56] References Cited

U.S. PATENT DOCUMENTS

| | | | |
|---|---|---|---|
| 1,994,932 | 3/1935 | Vidal | 422/122 |
| 2,337,357 | 12/1943 | Stuewer | 239/44 X |
| 2,587,949 | 3/1952 | Zodtner | 401/223 |
| 2,597,195 | 5/1952 | Smith | 422/125 |
| 2,802,695 | 8/1957 | Johnson | 239/44 |
| 2,804,291 | 8/1957 | Segerstad | 239/44 X |
| 2,847,976 | 8/1958 | Spaulding | 401/292 |
| 3,278,175 | 10/1966 | Hirtz | 261/99 |
| 3,283,787 | 11/1966 | Davis | 239/34 X |
| 3,379,855 | 4/1968 | Forrester et al. | 239/44 X |
| 3,550,853 | 12/1970 | Gray | 239/44 |
| 3,724,962 | 4/1973 | Hermring | 401/223 |
| 4,286,754 | 9/1981 | Jones | 239/6 |
| 4,413,779 | 11/1983 | Santini | 239/45 |
| 4,454,987 | 6/1984 | Mitchell | 239/6 |
| 4,768,676 | 9/1988 | Kaneko | 239/44 X |
| 4,913,350 | 4/1990 | Purzycki | 239/44 |
| 5,000,383 | 3/1991 | van der Heijden | 239/47 |
| 5,047,790 | 9/1991 | Cowger et al. | 347/87 |
| 5,121,881 | 6/1992 | Lembeck | 239/44 |

*Primary Examiner*—Lesley D. Morris

[57] ABSTRACT

This invention provides an air freshener dispenser device with a nonporous wicking feature, which in an operational mode consists of (a) a first container with an upside open end, (b) a second container which is inverted and internally-nested within the first container with a downside open end and an upside closed end, and with the sidewalls of the two containers in a capillary spacing proximity, (c) a top-surface closure in the first container which is a vapor-emanating surface mechanism, such as an absorbent matrix, that is in contact with the upside closed end of the nested second container, and (d) a content of air freshener medium confined within the nested second container. The capillary spacing proximity of the container sidewalls provides a nonporous wicking mechanism for transmission of the liquid air freshener medium from the interior reservoir to the vapor-emanating surface for evaporation into the atmosphere.

14 Claims, 1 Drawing Sheet

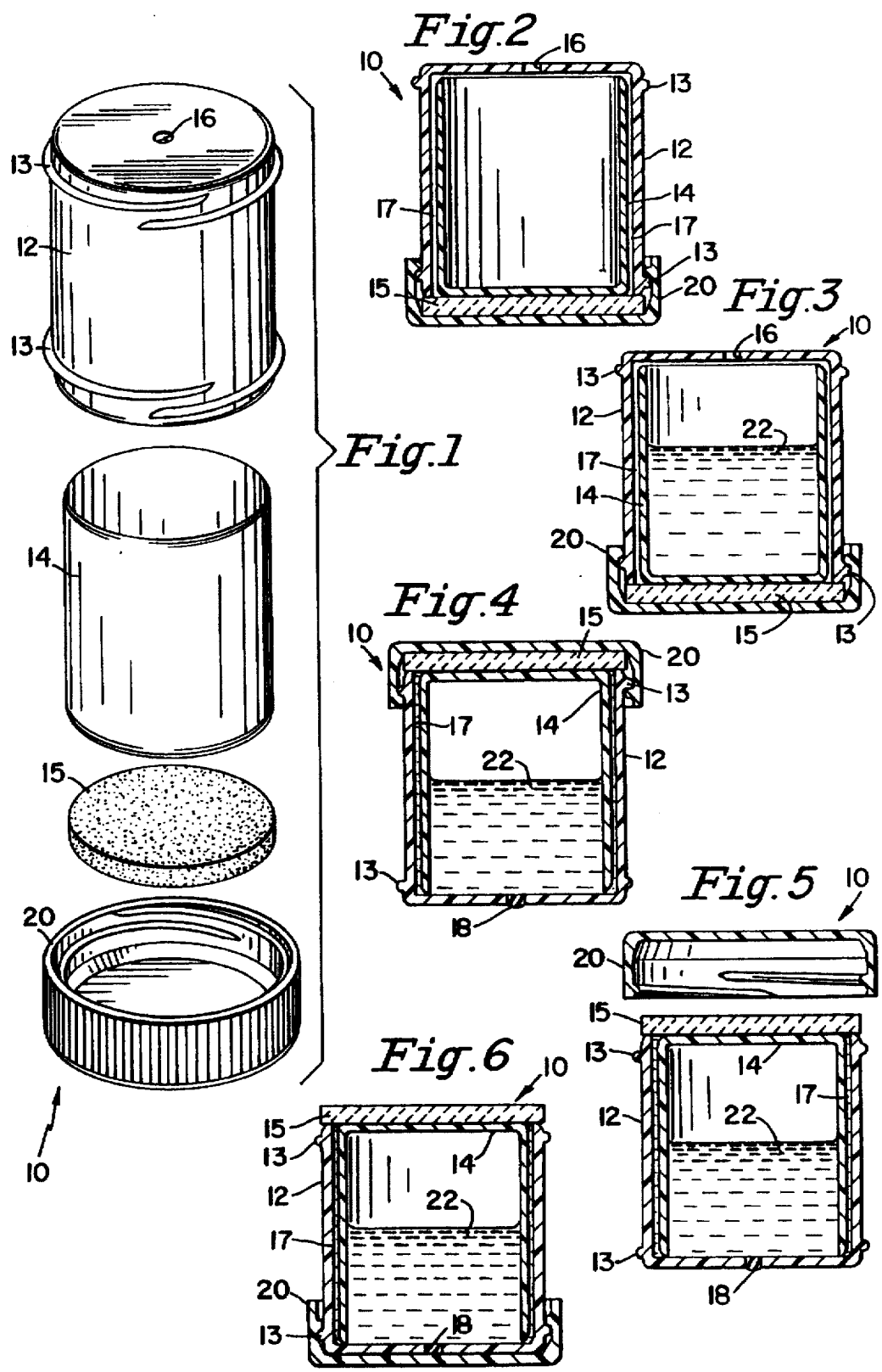

LIQUID AIR FRESHENER DISPENSER DEVICE WITH CAPILLARY WICKING MEANS

BACKGROUND OF THE INVENTION

This invention generally relates to dispensers of vaporizable media. More specifically, this invention relates to a device for dispensing a fragrance or deodorant in the form of a vapor for air freshening in an enclosed environment.

The need for effectively combating airborne malodors in homes and enclosed public buildings, by odor masking or destruction, is well established. Various kinds of vapor-dispensing devices have been employed for this purpose. The most common of such devices is the aerosol container which propels minute droplets of an air freshener composition into the air. Another common type of dispensing device is a dish containing or supporting a body of gelatinous matter which when it dries and shrinks releases a vaporized air-treating composition into the atmosphere. Other products such as deodorant blocks are also used for dispensing air-treating vapors into the atmosphere by evaporation. Another group of vapor-dispensing devices utilizes a carrier material such as paperboard impregnated or coated with a vaporizable composition.

A number of recent developments include a liquid air-treating composition in an enclosure, all or part of which is formed of a polymeric film through which the air-treating composition can migrate to be released as a vapor at an outer surface. Use of this type of permeable polymeric membrane controls the dispensing of air-treating vapors and tends to eliminate great variations in the rate of dispensing over the life of the product. Wicking devices are well known for dispensing volatile liquids into the atmosphere, such as fragrance, deodorant, disinfectant or insecticide active agent.

A typical wicking device utilizes a combination of a wick and emanating region to dispense a volatile liquid from a liquid reservoir. Wicking devices are described in U.S. Pat. Nos. 1,994,932; 2,597,195; 2,802,695; 2,804,291; 3,550,853; 4,286,754; 4,413,779; 4,454,987; 4,913,350; and 5,000,383; incorporated by reference.

Of special interest with respect to the present invention are wicking dispenser devices in which the wicking action is promoted by a nonporous wick structure. This type of device is described in U.S. Pat. Nos. 2,847,976; 3,283,787; 4,913,350; and 5,121,881; incorporated by reference.

Some air freshener dispensers are expensive to manufacture. Other air freshener dispensers are inexpensive to produce, but tend to have inferior construction and functionality.

There remains a need for a well-constructed air freshener dispenser device which can be mass-produced economically and which can deliver a vapor medium at a controlled uniform rate over an extended period of time.

Accordingly, it is an object of this invention to provide an improved air freshener dispenser device for delivering an odorant and/or deodorant vapor in an enclosed environment.

It is another object of this invention to provide an air freshener dispenser device with a primary structure which is a plastic assembly that can be produced economically by a thermoforming means.

It is another object of this invention to provide an air freshener dispenser device which has a novel assembly of vapor-emanating surface and liquid wicking means.

It is a further object of this invention to provide an air freshener dispenser device in which a liquid air freshener is transported from an enclosed reservoir to a vapor-emanating surface by capillary action with a nonporous wick structure.

Other objects and advantages of the present invention shall become apparent from the accompanying description and drawings.

SUMMARY OF THE INVENTION

One or more objects of the present invention are accomplished by the provision of an air freshener dispenser device comprising:

(a) a first sheer sidewall container with an upside open end, and a downside closed end having a porthole means accessing the container interior;

(b) a second sheer sidewall container which is inverted and internally-nested within the first container, with a downside open end and an upside closed end, wherein the coextensive sidewalls of the two containers are in a capillary spacing proximity;

(c) a top-surface closure in the first container which comprises a vapor-emanating surface means that is in contact with the upside closed end of the inverted internally-nested second container; and (d) a cover means which is removably attached to the first container, and which seals and isolates the vapor-emanating surface from the atmosphere.

In another embodiment this invention provides an air freshener dispenser device comprising:

(a) a first sheer sidewall container with an upper open end and a lower closed end;

(b) a second sheer sidewall container which is inverted and internally-nested within the first container, with a downside open end and an upside closed end, wherein the coextensive sidewalls of the two containers are in a capillary spacing proximity;

(c) a reservoir content of liquid air freshener medium which is confined within the interior volume of the internally-nested second container; and (d) a top-surface closure in the first container which comprises a vapor-emanating surface means that is in contact with the upside closed end of the internally-nested second container;

wherein the dispenser device is in an operational mode with the said capillary spacing proximity of the container sidewalls providing a wicking means for transmission of the liquid air freshener medium from the interior reservoir to the vapor-emanating surface for evaporation into the atmosphere.

DESCRIPTION OF THE DRAWINGS

FIG. 1 is a composite prospective view of an invention air freshener dispenser device which is in an inverted position.

FIG. 2 is a cross-sectional side view of a FIG. 1 invention dispenser device in assembled form.

FIG. 3 is a cross-sectional side view of a FIG. 2 invention dispenser device which has a reservoir content of liquid air freshener medium.

FIG. 4 is a cross-sectional side view of a FIG. 3 invention dispenser device which is in an upright position.

FIG. 5 is a cross-sectional side view of a FIG. 4 invention dispenser device with a detached screw-cap cover.

FIG. 6 is a cross-sectional side view of a FIG. 4 invention dispenser device with a screw-cap cover attached to the bottom end.

DESCRIPTION OF THE PREFERRED EMBODIMENTS

FIG. 1 illustrates an exploded view of present invention air freshener dispenser device 10 which is in an inverted position prior to charging with a liquid air freshener medium.

Air freshener dispenser device 10 as illustrated is composed of transparent semi-rigid thermoplastic container 12 which is cylindrical, and which has upper end and lower end threads 13 for engagement with cap 20. Porthole 16 is an access means to the interior of container 12. Porthole 16 is an optional feature to facilitate charging liquid medium into container 12.

Container 14 is of similar construction as container 12, and has dimensions adapted for internal-nesting within container 12. Absorbent matrix 15 as illustrated functions as a closure for the open end of container 12, as a vapor-emanating surface means.

FIG. 2 is a cross-sectional side view of a FIG. 1 invention dispenser device in assembled form. Container 14 is internally-nested within inverted container 12, with an upside open end and a downside closed end. The coextensive sidewalls of container 12 and container 14 have capillary spacing proximity 17.

Absorbent matrix 15 in FIG. 2 fits snugly within the open end of container 12, and is in contact with the downside closed end of internally-nested container 14. Cap 20 seals and isolates absorbent matrix 15 from the atmosphere.

FIG. 3 is a cross-sectional side view of a FIG. 2 invention device in which internally-nested container 14 has a reservoir content of liquid air freshener medium 22. The reservoir volume of container 14 is charged with air freshener medium 22 through porthole 16 in the upside closed end of inverted container 12. Air freshener medium 22 is in a reservoir zone within container 14.

FIG. 4 is a cross-sectional side view of a FIG. 3 invention dispenser device which is in an upright position, and which has sealed porthole 18 in the downside end surface of container 12. FIG. 4 illustrates a potentially operational invention device, with cap 20 sealing and isolating absorbent matrix 15 from the atmosphere.

FIG. 5 is a cross-sectional side view of a FIG. 4 invention dispenser device with cap 20 in a detached position. A FIG. 5 air freshener dispenser device 10 is fully operational. Liquid air freshener medium 22 is transmitted by capillary action through capillary spacing proximity 17 to absorbent matrix 15. Liquid air freshener medium 22 evaporates into the atmosphere from absorbent matrix 15. Typically capillary spacing proximity 17 is in the range between about 0.1–2 millimeters, and is in an interdependent hydrodynamic relationship with the surface tension properties of liquid air freshener medium 22.

FIG. 6 is a cross-sectional side view of a FIG. 4 invention device which has cap 20 attached to the downside closed end of container 12, where it serves as a base support for air freshener dispenser device 10.

Container 12 and container 14 can be constructed of the same or different thermoplastic compositions. Typically container 12 and container 14 are transparent structures which are injection or thermoform molded from a polymer such as polyethylene, polypropylene, polystyrene, polyvinyl acetate, polyamide, polymethacrylate, and the like. Container 12 and container 14 can be annular-shaped structures with vertical or slanted sidewalls, or they can be square or rectangular structures. Container 12 and container 14 can be any convenient design, with the proviso that the conformational sidewalls provide at least an effective degree of capillary spacing proximity 17, and internally-nested container 14 is in interacting contact with both absorbent matrix 15 and liquid air freshener medium 22.

Typically container 12 is a cylinder which has an interior diameter between about 1.5–5 centimeters, and a height between about 2–12 centimeters. The dimensions of internally-nested containers 14 are adapted to conform structurally with container 12, and to provide capillary spacing proximity 17.

Cap 20 can be an injection or thermoform molded structure of a polymer such as high density polyethylene or polypropylene. Cap 20 is secured to container 12 by a connecting means, such as a screw-on or snap-on feature. As illustrated in FIG. 5 and FIG. 6, air freshener dispenser device 10 is converted from a passive to an active operational mode by removal of cap 10 from its sealing and isolating juxtaposition with absorbent matrix 15. As a secondary function, cap 20 can be attached to the downside closed end of container 12, where it serves as a base support for air freshener dispenser device 10 while it is operational.

The vapor-emanating surface means, such as absorbent matrix 15, can be an organic or inorganic liquid-permeable structure, such as a thermoplastic, thermoset, cellulosic or ceramic composition. The dimensions of the vapor-emanating surface means can be adapted to frictionally secure the structure within the open end of container 12, and in contact with the upside closed end of internally-nested container 14.

Air freshener medium 22 in the FIGURES can be any air treating material which can be wicked up to absorbent matrix 15 by capillary action, and dispersed into the atmosphere in vapor form. Typically air freshener medium 22 is a fragrance or a deodorant formulation in liquid form.

Air freshener medium 22 preferably is a liquid fragrance comprising one or more volatile organic compounds which are available from perfumery suppliers such as Firmenich Inc., Takasago Inc., Noville Inc., Quest Co., and Givaudan-Roure Corp.

Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf , Cedar Wood, Geranium, Lavender, Orange, Origanum, Petitgrain, White Cedar, Patchouli, Lavandin, Neroli, Rose absolute, and the like.

A wide variety of chemicals are known for perfumery, such as aldehydes, ketones, esters, alcohols, terpenes, and the like. A fragrance can be relatively simple in composition, or can be a complex mixture of natural and synthetic chemical components.

A typical scented oil can comprise woody/earthy bases containing exotic constituents such as sandalwood oil, civet, patchouli oil, and the like. A scented oil can have a light floral fragrance, such as rose extract or violet extract. Scented oil also can be formulated to provide desirable fruity odors, such as lime, lemon or orange.

Synthetic types of fragrance compositions either alone or in combination with natural oils are described in U.S. Pat. Nos. 4,314,915; 4,411,829; and 4,434,306; incorporated herein by reference. Other artificial liquid fragrances include geraniol, geranyl acetate, eugenol, isoeugenol, linalool, linalyl acetate, phenethyl alcohol, methyl ethyl ketone, methylionone, isobornyl acetate, and the like.

Air freshener medium 22 also can be a liquid formulation containing a volatile pesticide such as p-dichlorobenzene, or a therapeutic a gent such as menthol.

Air freshener dispenser device 10 preferably is constructed of transparent or translucent materials, such that air freshener medium 22 is visible during usage for an indication of the liquid level in the interior reservoir of container 14.

A present invention air freshener dispenser device can be produced in high volume from relatively inexpensive plastic materials. After usage, the device qualifies for disposal as a non-hazardous solid waste.

What is claimed is:

1. An air freshener dispenser device comprising:
   (a) a first sheer sidewall container with an upside open end, and a downside closed end having a porthole means accessing the container interior;
   (b) a second sheer sidewall container which is inverted and internally-nested within the first container, with a downside open end and an upside closed end, wherein the coextensive sidewalls of the two containers are in a capillary spacing proximity;
   (c) a closure in the first container which comprises a vapor-emanating surface means that is in contact with the upside closed end of the inverted internally-nested second container; and
   (d) a cover means which is removably attached to the first container, and which seals and isolates the vapor-emanating surface from the atmosphere.

2. A dispenser device in accordance with claim 1 wherein the nested containers have conformational annular-shaped structures comprising a transparent thermoplastic composition.

3. A dispenser device in accordance with claim 1 wherein the vapor-emanating surface means comprises a liquid-permeable thermoplastic, thermoset, cellulosic or ceramic composition.

4. A dispenser device in accordance with claim 1 wherein the first container is structurally adapted to receive and secure the cover means at either end of the said first container.

5. A dispenser device in accordance with claim 1 wherein the cover means is a cap which is removably attached to the first container by screw-on or snap-on securing means.

6. A dispenser device in accordance with claim 1 wherein the device is inverted with the cover means positioned as a base support for the said device, and wherein the interior volume of the upright internally-nested second container is a reservoir with a content of liquid air freshener medium.

7. A dispenser device in accordance with claim 6 wherein the porthole means in the upside closed end of the first container is sealed after it has served as an access filling means for infusion of the liquid air freshener medium into the internally-nested second container reservoir.

8. A dispenser device in accordance with claim 1 wherein the porthole means is an optional feature.

9. An air freshener dispenser device comprising:
   (a) a first sheer sidewall container with an upside open end and a downside closed end;
   (b) a second sheer sidewall container which is inverted and internally-nested within the first container, with a downside open end and an upside closed end, wherein the coextensive sidewalls of the two containers are in a capillary spacing proximity;
   (c) a reservoir content of liquid air freshener medium which is confined within the interior volume of the internally-nested second container; and
   (d) a closure in the first container which comprises a vapor-emanating surface means that is in contact with the upside closed end of the internally-nested second container;

wherein the dispenser device is in an operational mode with the said capillary spacing proximity of the container sidewalls providing a wicking means for transmission of the liquid air freshener medium from the interior reservoir to the vapor-emanating surface for evaporation into the atmosphere.

10. A dispenser device in accordance with claim 9 wherein the nested containers have conformational annular-shaped structures comprising a transparent thermoplastic composition.

11. A dispenser device in accordance with claim 9 wherein the vapor-emanating surface means is an absorbent matrix comprising a liquid-permeable thermoplastic, thermoset, cellulosic or ceramic composition.

12. A dispenser device in accordance with claim 9 wherein the air freshener medium is a liquid fragrance composition.

13. A dispenser device in accordance with claim 9 wherein the air freshener medium is a liquid pesticide composition.

14. A dispenser device in accordance with claim 9 wherein the air freshener medium is a liquid therapeutic composition.

* * * * *